United States Patent [19]

Jenness

[11] Patent Number: 4,750,480
[45] Date of Patent: Jun. 14, 1988

[54] POSTURE-CORRECTING DEVICES

[76] Inventor: Lloyd Jenness, P.O. Box 1207, Perry, Fla. 32347

[21] Appl. No.: 29,104

[22] Filed: Mar. 23, 1987

[51] Int. Cl.⁴ .............................................. A61F 5/03
[52] U.S. Cl. ................................. 128/78; 128/101.1; 340/668
[58] Field of Search ................ 128/781, 782, 78, 774, 128/905; 340/573, 668; 2/44, 45, 338; 450/155

[56] References Cited

U.S. PATENT DOCUMENTS

| | | | |
|---|---|---|---|
| 2,681,955 | 6/1954 | Davis | 340/321 X |
| 3,582,935 | 6/1971 | Verhaeghe | 128/781 X |
| 3,608,541 | 9/1971 | Hall | 128/781 |
| 3,642,276 | 2/1972 | Kropf | 128/782 X |
| 3,670,320 | 6/1972 | Palmer | 340/573 |
| 4,007,733 | 2/1977 | Celeste et al. | 128/78 X |
| 4,191,949 | 3/1980 | Myers | 434/247 X |
| 4,392,126 | 7/1983 | Loyola | 128/782 X |

Primary Examiner—Robert A. Hafer
Assistant Examiner—Kevin Rooney
Attorney, Agent, or Firm—Millen & White

[57] ABSTRACT

Improvements in posture-correcting devices include a switch, wherein the switch has one contact mounted on an elastic length of material connected to a strap and the other contact connected to an inelastic pad. In addition, the improvements include readily detachable electrical circuits so that a circuit incorporating a particular type of signalling device can be selected for use.

8 Claims, 2 Drawing Sheets

POSTURE-CORRECTING DEVICES

BACKGROUND OF THE INVENTION

The instant invention related to improvements in posture-correcting devices. More particularly, the instant invention is directed to devices for encouraging a person to hold in their abdomen and devices for encouraging a person to hold the shoulders back.

To a large extent, correct posture is a matter of holding in one's abdomen and holding one's shoulders back and down in order to stand up straight without a slouching appearance. In many cases, control of the muscles which restrain the abdomen and shoulders against the force of gravity is possible through conscious effort. In that most people must occupy their minds with more than thoughts of good posture, several attempts have been made to cause people to shift those thoughts from conscious memory to unconscious memory. Exemplary of patents which reflect these attempts are U.S. Pat. Nos. 3,642,276; 4,191,949; 3,582,935; 4,007,733; and 4,055,168. Each of these patents discloses a belt-type device which emits signals when one's posture lapses. The first three patent listed are directed to devices for controlling the abdomen, while the last two patents disclose devices for controlling the shoulders or upper body.

As with any corrective or medical device which is worn by human beings, it is desirable to make the device as convenient, comfortable and unobtrusive as possible. Preferably, a posture control device should be configured to be worn beneath one's clothed without being either readily apparent to other people or uncomfortable to the person wearing the device. Moreover, it is preferable that such a device have a variety of indicating devices selectable by the person using the device.

SUMMARY OF THE INVENTION

It is an object of the instant invention to provide a new and improved posture-correcting device which is comfortable to wear, unobtrusive when worn under clothes and adaptable to the particular needs of various people.

In view of the aforementioned objects, the instant invention contemplates apparatus for correcting posture and maintaining correct posture of a person by utilizing a pad made of nonstretchable, flexible fabric for extension across a portion of a person's body. The pad is held in place by a strap which is secured by a length of elastic material to one end of the pad and detachably fastened to the other end of the pad. A switch having first and second contacts is provided, the switch having the first contact on the pad and the second contact secured to the elastic material which attaches one end of the strap to the pad. The strap is releasably fastened to the other end of the pad so as to position the contacts out of engagement as long as the person wearing the device maintains correct posture. Upon the person relaxing their abdomen or slouching their shoulders (depending on which embodiment of the invention is being used), the first and second contacts engage one another allowing a circuit to be closed. Upon closing the circuit, a signalling device such as a beeper, tactile vibrator or mild electrical shock reminds the individual to correct his or her posture.

In accordance with a preferred embodiment of the invention, the electrical circuit is mounted on a detachable panel wherein the detachable panel is connected to the switch via a plug-type electrical connector, wherein the panel may have a selected signal device with either a tactile or audible signal.

In accordance with one embodiment of the invention, the device is used to correct protruding abdomens, and in accordance with still another embodiment of the invention, the device is used to correct slouching shoulders.

Upon further study of the specification and appended claims, further objects and advantages of this invention will become apparent to those skilled in the art.

DETAILED DESCRIPTION

Figure 1:
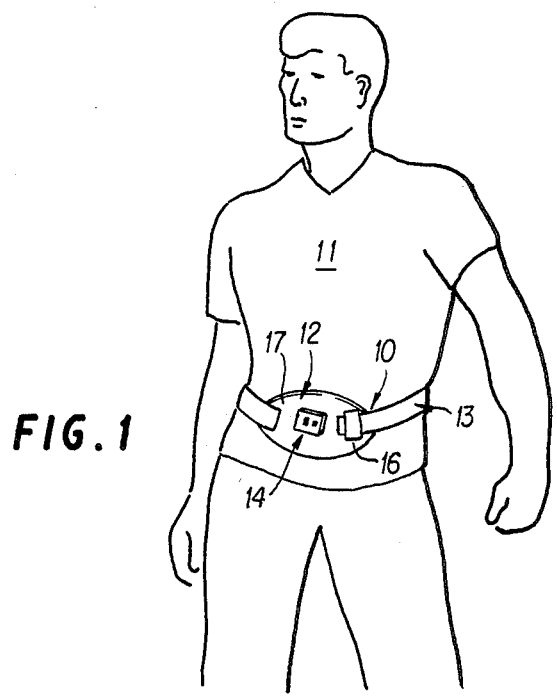
FIG. 1 is a perspective view of a person wearing a device in accordance with the instant invention to control protruding of his abdomen.

Referring now to FIG. 1, there is shown a posture-correcting device, designated generally by the numeral 10, configured in accordance with the principles of the instant invention for causing a person 11 to subconsciously hold in his or her abdomen and thus maintaining a flat stomach. The device comprises a pad, designated generally by the numeral 12, to which an inelastic belt or strap, designated generally by the numeral 13, is connected and on which is mounted an electrical circuit, designated generally by the numeral 14. The pad 12 fits over the abdomen and is made of a flexible, nonstretchable material. The pad 12 has a first end 16 and a second end 17.

Figure 3:
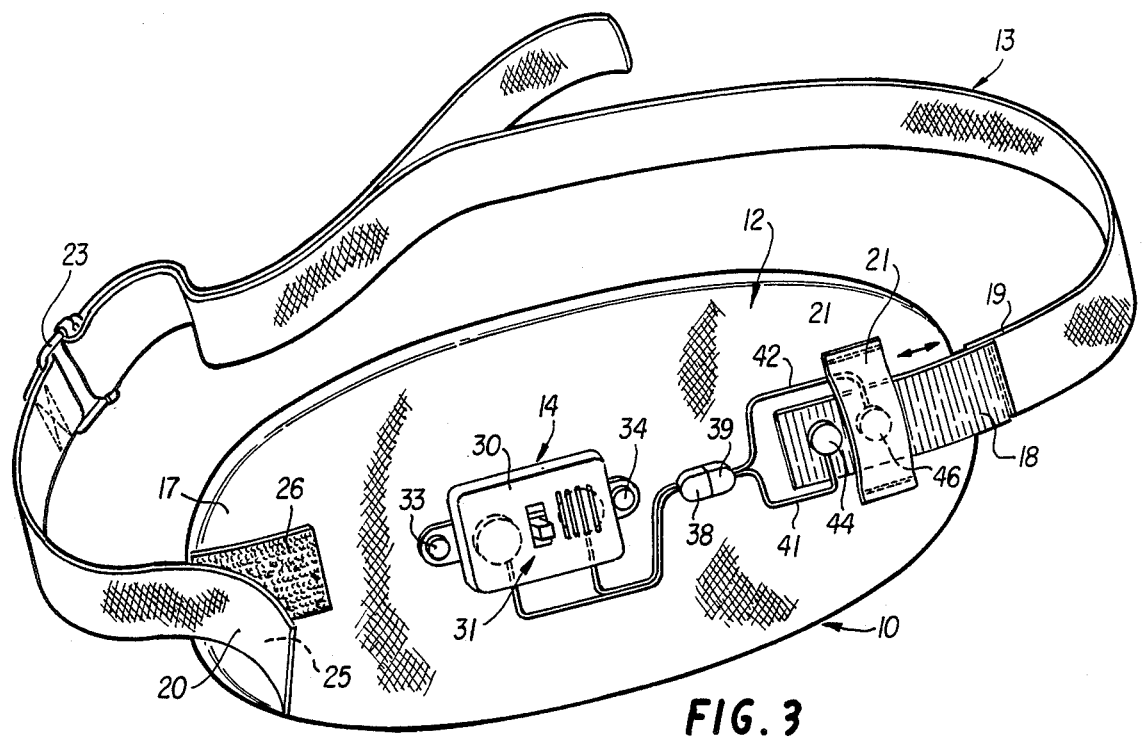
FIG. 3 is a perspective view of the device of FIG. 1 configured as a belt.
Figure 4:
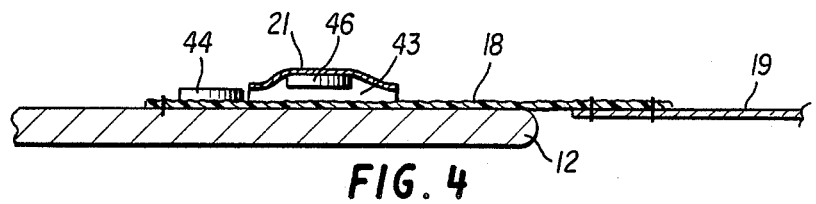
FIG. 4 is a cross-section through the device of FIG. 3 showing the position of contacts when the abdomen is held in or, with respect to FIG. 2, when the shoulders are held back.
Figure 5:
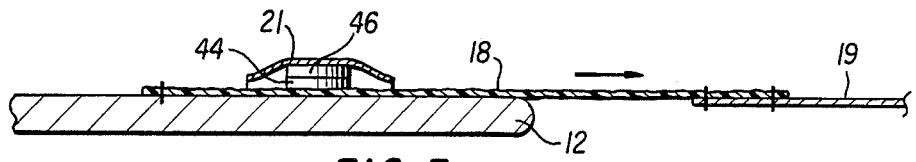
FIG. 5 is a cross-section similar to FIG. 4 only showing the contacts engaged indicating that the wearer's abdomen is protruding or that their shoulders are slouching.

Referring now to FIG. 3, the inelastic strap 13 has a length of elastic material 18 fixed at a first end 19 of the strap and has a second end 20 attached to the pad 12 at a location inboard from the end 17 of the pad. A loop of inelastic material 21 is secured at both ends to the pad 12 and bridges the elastic material 18. Intermediate the first end 19 of the inelastic strap 13 and the second end 20 of the inelastic strap, there is an adjustable buckle 23. The second end of the belt 20 has one component of a VELCRO fastener (perhaps the hooks thereof) 25 fixed thereto which fastens to a complementary second portion of a VELCRO fastener (perhaps the loops thereof) 26 which second portion is fixed to the pad 12.

Figure 6:
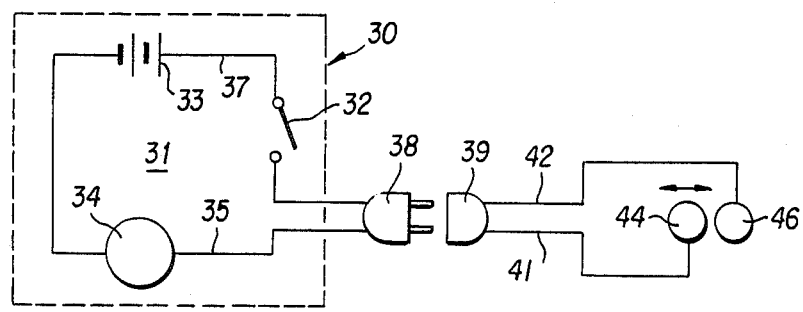
FIG. 6 is a circuit diagram illustrating an indicating circuit in accordance with the instant invention.

A panel 30 for mounting the elements, designated generally by the numeral 31, of the electrical circuit 14 is detachably secured to the pad 12 by snap fasteners 47 and 48. As is seen in FIG. 6, the circuit 31 includes a battery 33, and a manual on-off switch 32 and a signalling device 34 connected via leads 35, 36 and 37. Leads 36 and 37 have a plug 38 thereon which connects to a jack 39 so that the circuit 31 can be selectively detached from the pad 12 with the circuit panel 30. The jack is fixed to the panel 12 and has leads 41 and 42 extending therefrom. Lead 41 is connected to a first contact 44 mounted on the length of elastic material 18 while lead 42 is connected to a second contact 46 mounting on the band 21 which fits over the length of elastic material 18. When the elastic material 18 is relaxed, the contact 44 is between attachment area 20 and the band 21 so as to be inboard of the band. However, if the elastic 18 is stretched, the first contact 44 becomes aligned with and in contact with the second contact 46, thus closing the circuit of the switch 43. When the switch 43 is closed, the battery 33 energizes the indicator 34 so that a signal is generated.

In using the posture-correcting device 10, the person 11 wearing the device contracts his muscles and in order to pull in his abdomen. The abdominal pad 12 is placed over his abdomen and the VELCRO fastener 25-26 is attached with without stretching the elastic material 18 of by stretching the elastic material 18 by only an amount which is insufficient to align the contacts 44 and 46. If necessary, the adjustable buckle 23 is adjusted to determine the length of the inelastic strap 13. When the abdominal muscles of the person 11 wearing the posture-correcting device 10 relax, the length of elastic material 18 stretches and the contacts 44 and 46 come into alignment, close the switch 43 and energize the indicator 34. When the indicator 34 emits its signal, the person 11 stops the signal by tightening his abdominal muscles. After a number of warnings by the signalling device 34, the person "learns" to keep his or her stomach muscles taught. After a while, the person's subconscious takes over and the person tends to continuously hold his or her stomach muscles tight even when not wearing the posture-correcting device 10.

The indicator 34 is selectable and may be an audible buzzer, a mechanical vibrator, or a device which emits a mild electrical shock just sufficient to remind the person without any particular unpleasantness. The type of reminder can be selected by simply selecting the panel 30 having the desired indicator 34 thereon and connecting the circuit 31 to the switch by plugging plug 38 into jack 39.

Figure 2:
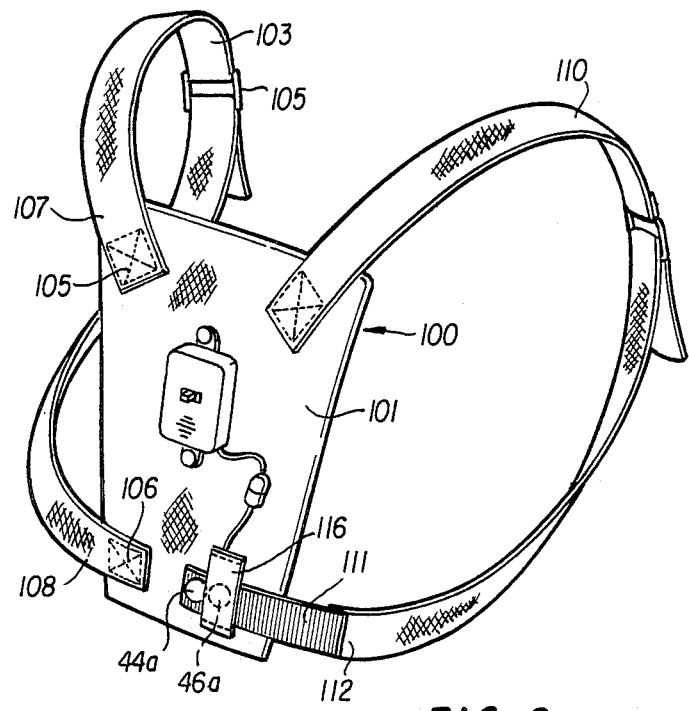
FIG. 2 is a perspective view of a device in accordance with the instant invention for correcting slouching shoulders.

Referring now to FIG. 2, a second embodiment of the instant invention is disclosed in the form of a shoulder harness, designated generally by the numeral 100. The harness 100 has components and follows principles analogous to those of the abdominal device 10 of FIGS. 1 and 3-6. With the shoulder device 100, a back pad 101 is provided for mounting one of the circuit panels 30 detachably thereon. The panel 30 has the same electrical circuit 31 as the abdominal control device 10. A first inelastic strap 103 is attached to a first side of the back pad 101 by stitches 105 and 106 at first and second ends 107 and 108 of the strap, respectively. The strap 103 is stitched to the pad 101 with the same surface facing the pad. In addition, the strap 103 has an adjustable buckle 105 thereon so that the length of the strap can be readily adjusted. A second inelastic strap 110 is attached at one end to the opposite side of the back pad 101 by a length of elastic material 111 stitched to a first end 112 of the strap and is directly stitched to the back pad at the opposite end thereof. As with the abdominal device 10, the shoulder harness 100 utilizes a band 116 which straddles the elastic portion 111 of the second belt 110. A first contact 44a is positioned on the length of elastic material 111 while s second contact 46a is positioned on the band 116. When the wearer's shoulder relax, the contacts 44a and 46a close so as to energize indicator 34 with current from battery 33 (see FIG. 6).

In each of the embodiments, the electrical components are on the outside of the pads 101 and 102 so as to not press uncomfortably against the wearer. In addition, the electrical component are relatively flat so as to be easily concealed by clothing.

From the foregoing description, one skilled in the art can easily ascertain the essential characteristics of the invention and, without departing from the spirit and scope thereof, can make various changes and modifications of the invention to adapt it to various usages and conditions.

What is claimed is:

1. Apparatus extendable around the body of a person for improving the posture of the person, the apparatus including:

a pad made of nonstretchable, flexible fabric, the pad having first and second ends and extending across the body of the person; the pad having a band of material having opposite ends secured to the pad defining a space between the band, ends of the band and pad;

strap means having first and second ends, the first end of the strap means being permanently secured to the first end of the pad with a length of elastic material which passes through the space defined by the band; the second end of the strap means having means thereon for detachably securing the second end of the strap means to the second end of the pad, whereby the pad is held in engagement with the person's body by the strap which extends around the back of the person;

a switch having first and second contacts, the first contact being mounted on the elastic material for movement therewith as the elastic material stretched and the second contact being secured to the band on the pad, wherein when the elastic material stretches, the contact thereon slides into engagement with the contact on the band and the switch is electrically closed; and an electrical circuit connected to the switch, the electrical circuit having indicator means connected therein for activation upon closing the switch.

2. The apparatus of claim 1 further including a relatively stiff panel for mounting the electrical circuit on the pad and an electrical connector having one portion connected permanently to the switch on the pad and another portion detachably from the first portion connected to the electrical circuit on the stiff panel.

3. The apparatus of claim 2 wherein the circuit includes a battery, the battery and indicator being mounted on the panel.

4. The apparatus of claim 3 wherein the indicator emits an audible signal when activated.

5. The apparatus of claim 3 wherein the indicator emits an tactile signal when activated.

6. The apparatus of claim 1 wherein the fastening means comprises complementary VELCRO surfaces on the second ends of the strap and pad, respectively.

7. The apparatus of claim 1 wherein the strap means comprises a single belt for encircling the waist of the person wearing the apparatus wherein, when the person's abdomen sags, the length of elastic material expands closing the contacts of the switch and activating the indicating means.

8. The apparatus of claim 1 wherein the strap means comprises a pair of belts for fitting around the wearer's shoulders, and wherein the pad is positionable on the back of the person wearing the apparatus, one of the belts being attached to the pad by the length of elastic material with the first contact of the switch thereon, the second contact being on the pad, wherein when the shoulders of the person wearing the apparatus sag, the contacts are closed and the indicator means notifies the person that his shoulders are sagging by emitting a signal.

* * * * *